US005420473A

United States Patent [19]

Thomas

[11] Patent Number: 5,420,473

[45] Date of Patent: May 30, 1995

[54] SPARK GAP ELECTRODE ASSEMBLY FOR LITHOTRIPTERS

[76] Inventor: Howard C. Thomas, 10330 N. Meade Loop, Westminster, Colo. 80030

[21] Appl. No.: 134,913

[22] Filed: Oct. 12, 1993

[51] Int. Cl.[6] ........ A61B 17/22

[52] U.S. Cl. ........ 313/141

[58] Field of Search ........ 313/141-146, 313/119, 122, 125; 123/169 EA, 169 EC, 169 E, 169 P; 601/4

[56] References Cited

U.S. PATENT DOCUMENTS

| | | | |
|---|---|---|---|
| 2,559,227 | 7/1951 | Rieber | 128/4 |
| 3,728,671 | 4/1973 | Poston | 340/12 SD |
| 3,942,531 | 3/1976 | Hoff et al. | 128/328 |
| 3,970,076 | 7/1976 | Hepp et al. | 128/24.5 |
| 4,608,983 | 9/1986 | Muller et al. | 601/4 |
| 4,809,682 | 3/1989 | Forssmann et al. | 601/4 |
| 4,905,673 | 3/1990 | Pimiskern | 128/24 |
| 4,905,674 | 3/1990 | Nowacki et al. | 128/328 |
| 4,934,353 | 6/1990 | Nowacki et al. | 601/4 |
| 4,938,781 | 7/1990 | Pimiskern | 601/4 |
| 5,047,685 | 9/1991 | Nowacki et al. | 313/141 |

FOREIGN PATENT DOCUMENTS

| | | | |
|---|---|---|---|
| 3844419A | 7/1989 | Germany | 601/4 |
| 457037A | 11/1991 | Germany | 601/4 |

*Primary Examiner*—Edward L. Coles, Sr.

*Assistant Examiner*—Jerome Grant, II

*Attorney, Agent, or Firm*—Dorr, Carson, Sloan & Birney

[57] ABSTRACT

A spark gap electrode assembly for lithotripters allows easy replacement of both electrode tips without requiring manual adjustment of the spacing between the tips. The electrode assembly uses a housing with a conductive cage extending from its distal end to support the grounded electrode. The cage holds the base of the grounded electrode so that the tip of the grounded electrode is located at a predetermined position relative to the distal end of the housing. The discharge electrode assembly is threaded through a passageway in the housing extending along a longitudinal axis. The discharge electrode assembly includes an elongated conductive body with a proximal end for connection to an external electrical power supply and a tip at its distal end. An insulative layer covers the discharge electrode between its tip and proximal end. The insulative layer also includes a stop to prevent further insertion of the discharge electrode assembly beyond a predetermined position within the housing passageway so that the tip of the discharge electrode extends through the distal end of the housing to a location separated by a predetermined distance from the tip of the grounded electrode. In the preferred embodiment, the cage includes an end cap having a passageway and a setscrew to removably secure the grounded electrode in place.

14 Claims, 5 Drawing Sheets

SPARK GAP ELECTRODE ASSEMBLY FOR LITHOTRIPTERS

BACKGROUND OF THE INVENTION

1. Field of the Invention

The present invention relates generally to the field of lithotripters used for noninvasive fragmentation of concrements in living beings. More specifically, the present invention discloses an improved spark gap electrode for lithotripters in which the discharge electrode tip can be readily removed and a replacement tip installed with precise mechanical positioning.

2. Statement of the Problem

Conventional extra-corporeal lithotripters utilize shock waves to noninvasively fragment concrements within a patient (e.g., renal and ureteral calculi located primarily in the upper urinary tract). Conventional lithotripters comprise a truncated ellipsoidal reflector. The reflector is filled with a liquid, e.g., water, that couples the interior of the reflector to the patient's body, and through the tissues of the body to the concrement to be destroyed. The reflector is provided with a spark gap at the first focal point of the ellipsoid. The concrement is positioned coincident with the second focal point of the reflector by means of x-ray or ultrasound imaging. An electrical discharge across the electrodes of the spark gap causes a certain amount of water to be flashed into steam, accompanied by generation of a shock wave. This shock wave is focused by the ellipsoidal reflector on the second focal point, and hence on the concrement. A rapid succession of such sparks is sufficient to substantially disintegrate any concrement.

However, the rapid and frequent discharge of energy across the electrode tips of the spark gap also causes rapid erosion and deterioration of the electrode tips. Spark gap electrodes typically last no longer than one treatment and often must be changed during treatment. The conventional solution to this problem is to frequently replace the entire electrode assembly. For example, a side cross-sectional view of the prior art spark gap electrode assembly produced by Medstone is shown in FIG. 5. FIG. 6 is a side cross-sectional view of the prior art spark gap electrode assembly produced by Dornier. The Dornier device does not provide a means for replacing the electrode tips. The Medstone device can be rebuilt with substantial difficulty, but replacement of the electrode tips is relatively complicated, cumbersome, and requires manual calibration of the gap between the electrode tips.

Other prior art spark gap electrode assemblies include means for periodically adjusting the spacing between the electrode tips to compensate for burn-off during use. This approach requires a complicated mechanical arrangement to allow the electrode tips to be regapped in place. Such devices are relatively expensive. The regapping process is time consuming, subject to error, and can result in inferior mechanical and/or electrical properties for the device.

In particular, a number of spark gap electrode assemblies have been invented in the past, including the following:

| Inventor | Patent No. | Issue Date |
|---|---|---|
| Nowacki et al. | 5,047,685 | Sept. 10, 1991 |
| Nowacki et al. | 4,905,674 | March 6, 1990 |
| Pimiskern | 4,905,673 | March 6, 1990 |
| Müller et al. | 4,608,983 | Sept. 2, 1986 |
| Hepp et al. | 3,970,076 | July 20, 1976 |
| Hoff et al. | 3,942,531 | March 9, 1976 |
| Poston | 3,728,671 | Apr. 17, 1973 |
| Rieber | 2,559,227 | July 3, 1951 |

The patents of Nowacki et al. disclose two examples of electrode structures for a lithotripter.

Pimiskern discloses an arc discharge device for shock wave generation wherein the two electrodes 4, 6 have flattened tips of different diameters.

Müller et al. disclose a shock wave generator for breaking up concrements (e.g., kidney stones, gallstones, or bladder stones) within a living body. The device has an ellipsoidal reflection chamber having two focal points, one to be aligned with the concrement to be destroyed and the other located in a spark discharge path between two electrodes. One of the electrodes 36 is a point-like extension of an inner conductor. The outer conductor carries several flat arch-shaped holders to position the other electrode. A threaded mounting arrangement allows the two electrodes to be moved toward and away from each other to compensate for burn-off of the electrodes during use. Two mounts 64 and 66 hold the electrodes in a chuck-like fashion to facilitate easy replacement of the electrodes. The small size of the mounts would require tiny electrodes that are subject to rapid burn-off during use. In addition, fine adjustment and initial calibration of the electrode spacing would be required.

Hepp et al. disclose an apparatus for heart stimulation using pressure waves produced by a spark discharge within an elliptical coupling chamber.

Hoff et al. disclose another example of a shock wave generator for breaking up concrements within a living body. This apparatus uses a spark gap at one focal point within an elliptical waveguide.

Poston discloses a multiple-electrode directional acoustic source. Concentric electrode pairs of opposite polarity improve the efficiency of a spark gap acoustic source for marine seismic profiling. One electrode of each pair is tubular. The other electrode is rod-like and positioned axially within the tubular electrode.

Rieber discloses another example of a shock wave generator using a spark gap at one focal point within an ellipsoid shell.

3. Solution to the Problem

None of the prior art references uncovered in the search show a spark gap electrode for lithotripters that allows the electrode tips to be easily and quickly removed and replacement tips installed with precise mechanical positioning. Manual calibration or adjustment of the gap between the electrode tips is not required.

SUMMARY OF THE INVENTION

This invention provides a spark gap electrode assembly for lithotripters that uses a housing with a conductive cage extending from its distal end to support the grounded electrode. The cage holds the base of the grounded electrode so that the tip of the grounded electrode is located at a predetermined position relative to the distal end of the housing. The discharge electrode assembly is threaded through a passageway in the housing extending along a longitudinal axis. The discharge electrode assembly includes an elongated conductive body with a proximal end for connection to an external electrical power supply and a tip at its distal end. An insulative layer covers the discharge electrode between its tip and proximal end. The insulative layer also includes a stop to prevent further insertion of the discharge electrode assembly beyond a predetermined position within the housing passageway so that the tip of the discharge electrode extends through the distal end of the housing to a location separated by a predetermined distance from the tip of the grounded electrode. In the preferred embodiment, the cage includes an end cap having a passageway and a setscrew to removably secure the grounded electrode in place.

A primary object of the present invention is to provide an improved spark gap electrode assembly that facilitates rapid and inexpensive replacement of the electrode tips while maintaining superior mechanical tolerances and electrical properties compared with prior art devices.

Another object of the present invention is to provide an improved spark gap electrode assembly utilizing a discharge electrode encapsulated in a nonconductive mechanical assembly that incorporates means for precise mechanical alignment with respect to the opposing grounded electrode tip so that replacement of both electrodes can be quickly accomplished to exacting tolerances.

Yet another object of the present invention is to provide an improved spark gap electrode assembly in which the discharge electrode is encapsulated in an insulating material having a predetermined shape and dimensions such that the discharge electrode can be rapidly removed and a replacement accurately installed in the assembly without the need for calibration.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
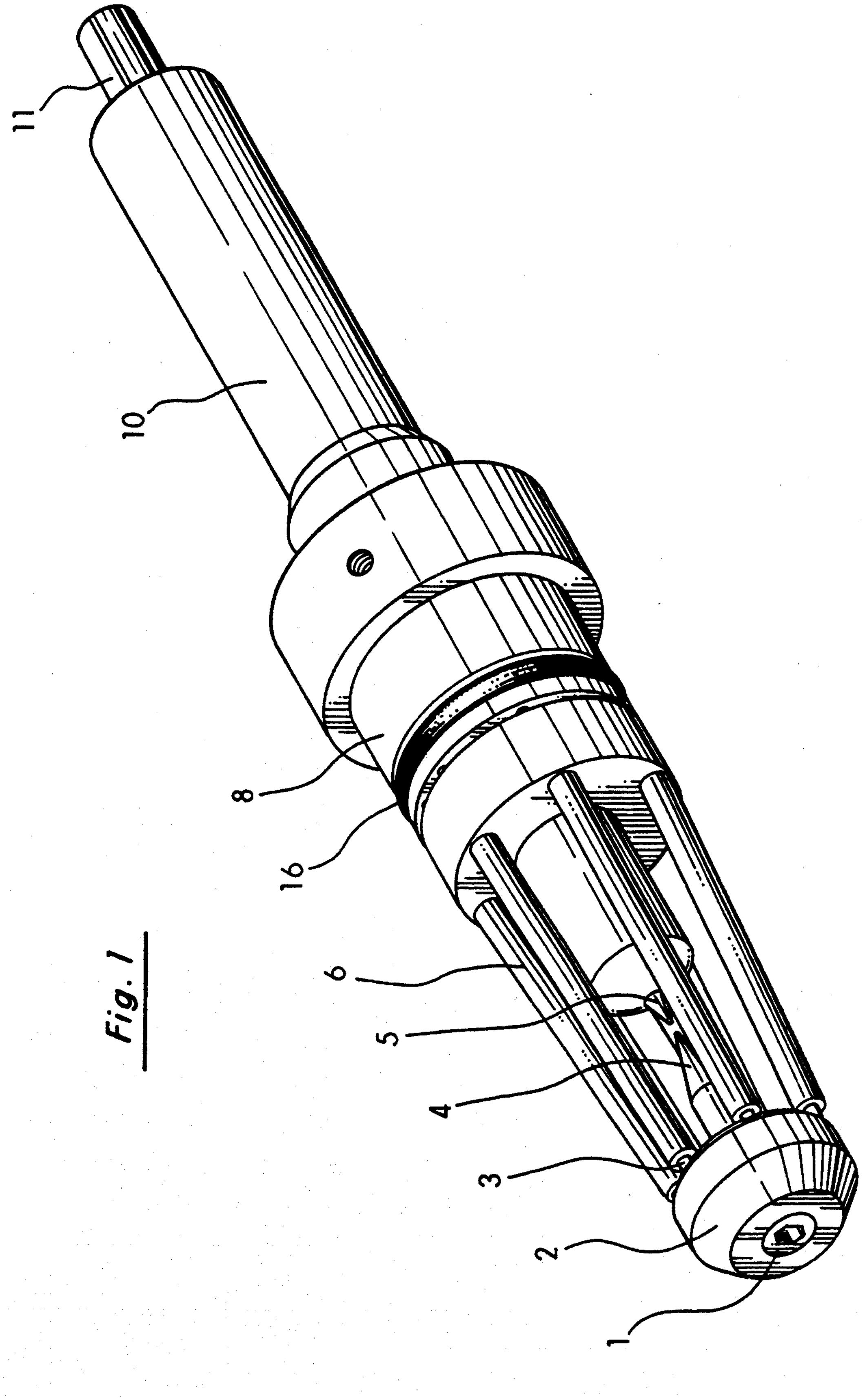
FIG. 1 is a perspective view of the entire electrode assembly.

Turning to FIG. 1, a perspective view is provided of the entire spark gap electrode assembly. FIG. 4 is a side cross-sectional view of the spark gap electrode assembly corresponding to FIG. 1. The first major subassembly of the device includes the housing 8, electrode discharge cage 3 and 6, grounded electrode 4, and end cap 2 shown in side cross-sectional view in FIG. 3. The other major component is the discharge electrode assembly, which includes the discharge electrode 5, 11, and 14 and its insulative layer 10 shown in side cross-sectional view in FIG. 2.

Figure 3:
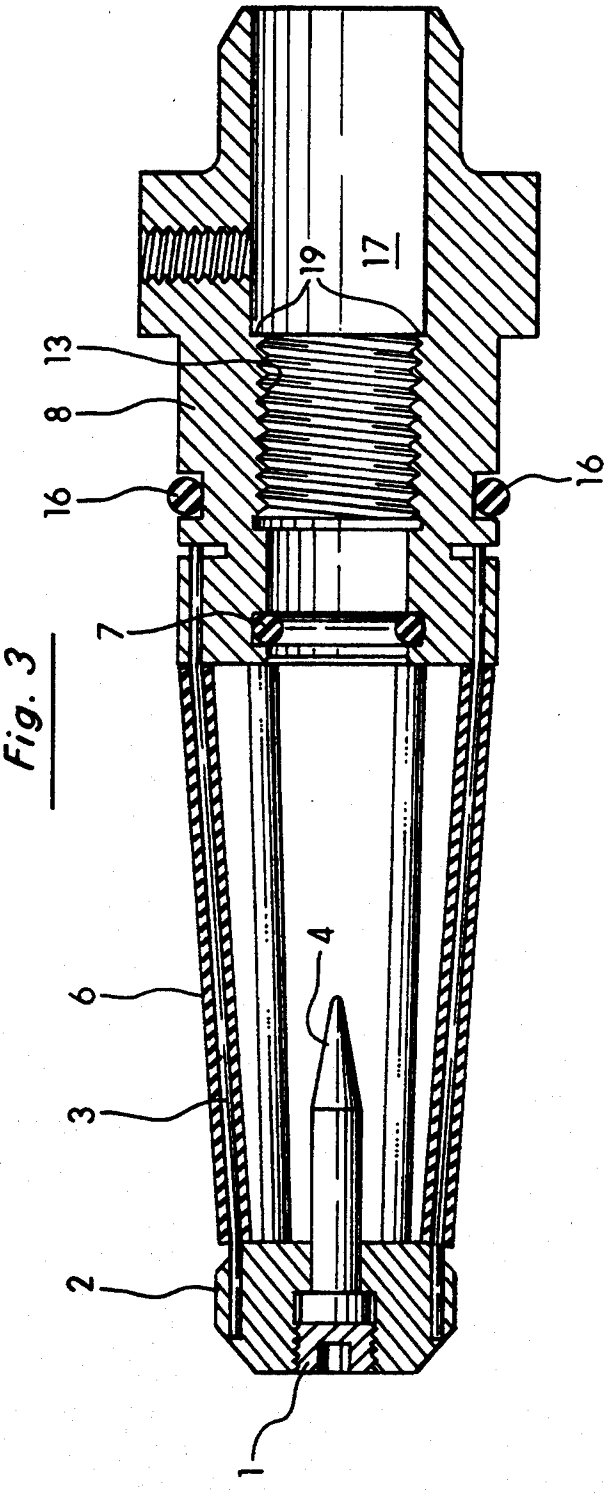
FIG. 3 is a side cross-sectional view of the discharge electrode assembly.
Figure 2:
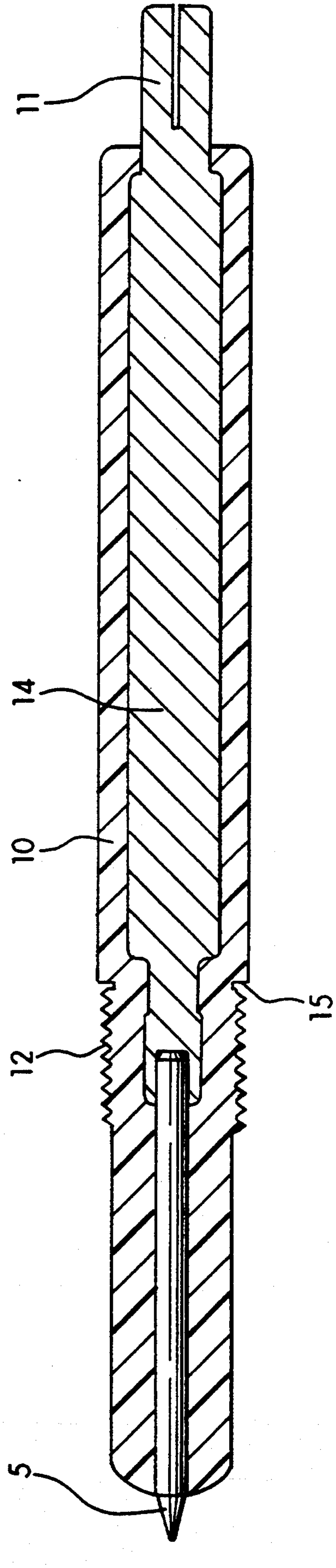
FIG. 2 is a side cross-sectional view of the electrode discharge cage, the grounded electrode tip, and the end cap supporting the base of the grounded electrode.
Figure 4:
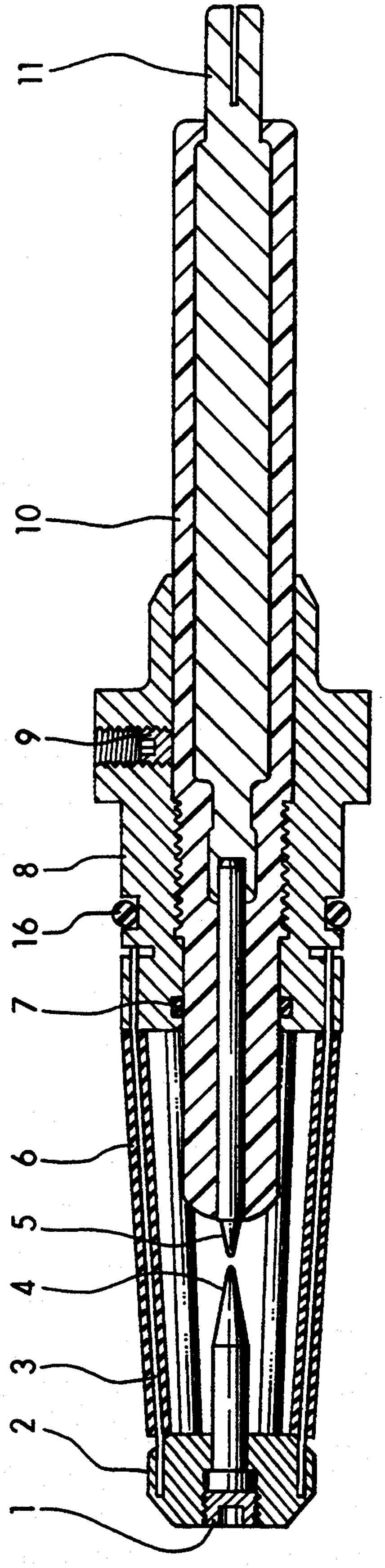
FIG. 4 is a side cross-sectional view of the entire electrode assembly corresponding to FIG. 1.
Figure 5:
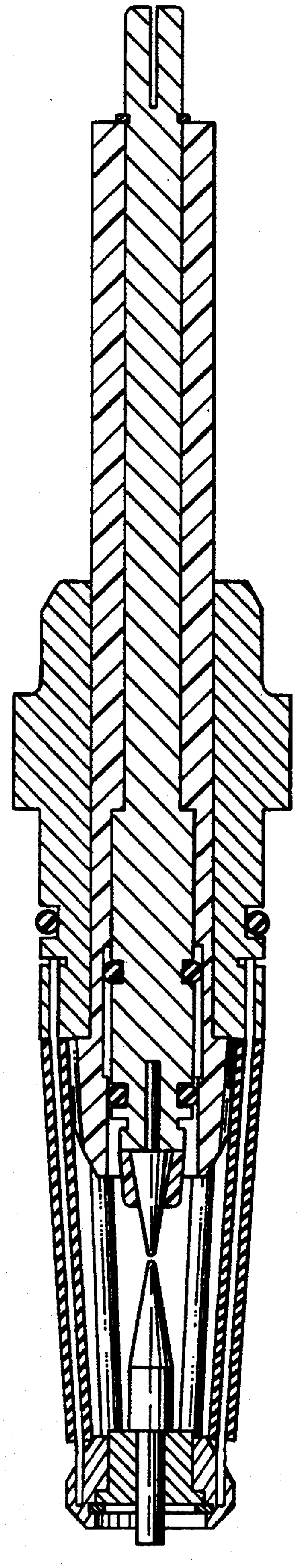
Fig. 5 (Prior Art)
FIG. 5 is a side cross-sectional view of the Medstone prior art electrode assembly.
Figure 6:
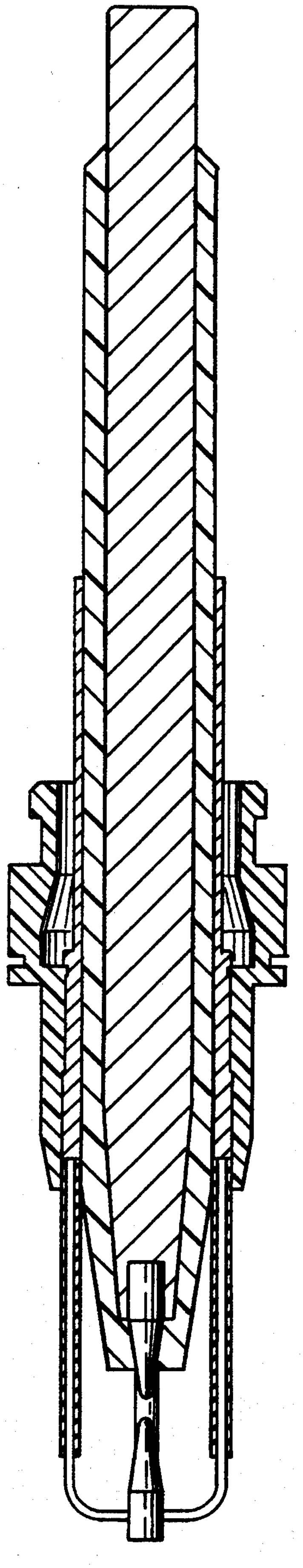
Fig. 6 (Prior Art)
FIG. 6 is a side cross-sectional view of the Dornier prior art electrode assembly.

The housing 8 has an internal passageway 17 extending along a longitudinal axis between a distal opening shown at the left side and a proximal opening shown at the right side of FIG. 3. The housing passageway 17 also has a locating shoulder 19 with a reduced diameter located at a precisely predetermined position relative to the distal opening of the housing. Alternatively, an inwardly extending lip, edge, protrusion, or other type of stop can be employed. In the preferred embodiment, the housing passageway 17 also has interior threads 13 to engage corresponding threads 12 on the insulative layer 10 of the discharge electrode assembly as shown in FIG. 2, and as will be discussed below in greater detail. An interior O-ring 7 within the passageway 17 provides a fluid-tight seal between the housing 8 and the discharge electrode assembly. A second O-ring 16 can be included on the exterior of the housing to provide a fluid-tight seal between the exterior of the housing 8 and the remainder of the lithotripter reflector.

A cage extends from the distal end of the housing 8 as shown in FIGS. 1, 3 and 4. This cage is formed by a plurality of support wires 3, each of which is surrounded by an insulating coating 6. The wires 3 support an end cap 2 at a predetermined location relative to the distal opening of the housing passageway 17, and also provide an electrical path to an external ground for the end cap.

The end cap 2 is made of an electrically conductive material. It includes a passageway 1 extending through the end cap 2 along the same axis as the housing passageway 17 to hold the base of the grounded electrode 4 as shown in FIG. 3. In the preferred embodiment shown in the drawings, the grounded electrode 4 has an enlarged base and the end cap passageway 1 has a locating shoulder with a reduced diameter that contacts and retains the base of the grounded electrode 4. Alternatively, an inwardly extending lip, protrusion, edge, or stop can be employed to retain the base of the grounded electrode 4 within the end cap passageway 1. The tip of the grounded electrode 4 passes through the end cap to a predetermined location relative to the distal opening of the housing passageway 17. The dimensions of the cage, end cap, and grounded electrode and the position of the shoulder within the end cap passageway are all carefully selected within tight tolerances to precisely fix the position of the tip of the ground electrode relative to the remainder of the housing. A removable setscrew, clip, or pin is used to secure the base of the grounded electrode 4 against this shoulder within the end cap passageway. In the preferred embodiment shown in the drawings, the end cap passageway 1 has internal threads, and a setscrew is threaded into this passageway 1 to secure the base of the grounded electrode 4 against the shoulder of the end cap 2.

The discharge electrode assembly includes an elongated high-voltage conductor 14 with a tip 5 at its distal end and a connector 11 at its proximal end for connection to an external electrical power supply. The body of the discharge electrode is covered with an insulative layer 10 that leaves the tip 5 and connector 11 of the discharge electrode exposed. This insulative layer 10 is made of molded plastic in the preferred embodiment. Retaining threads 12 are formed in the outer surface of the insulative layer 10 as shown in FIG. 2. These retaining threads 12 are sized and configured to engage the threads 13 within the housing passageway 17 when the discharge electrode assembly is inserted into the housing passageway 17. In addition, the exterior surface of the insulative layer includes a raised shoulder having an increased diameter that comes into contact with the locating shoulder 19 within the housing passageway 17 when the discharge electrode assembly is inserted into the housing. Alternatively, an outwardly extending edge, protrusion, or other stop 15 can be used for this purpose.

During initial assembly of the device, the grounded electrode 4 is inserted through the passageway 1 in the end cap 2 until the enlarged base of the grounded electrode 4 abuts the shoulder within the end cap passageway. This ensures that the tip of the grounded electrode 4 is precisely located in the desired position relative to the distal opening in the housing 8. The grounded electrode 4 can then be secured in place by tightening a setscrew or other equivalent locking means. The discharge electrode assembly is inserted into the housing passageway 17 through its proximal opening. The discharge electrode assembly can be freely inserted up to the point where the retaining threads 12 on the outer surface of the insulative layer 10 begin to engage the interior threads 13 within the housing passageway 17. Thereafter, the user must rotate the discharge electrode assembly about its longitudinal axis relative to the housing 8 to cause the threads 12 and 13 to engage one another. The tip 5 of the discharge electrode gradually emerges from the distal opening of the housing and approaches the tip of the grounded electrode 4 along the longitudinal axis as these threads engage. The internal O-ring 7 gradually forms a fluid-tight seal between the insulative layer 10 and the housing passageway 17 as the discharge electrode assembly is inserted. Forward progress can continue until the raised shoulder or stop 15 of the discharge electrode assembly comes into contact with the shoulder or stop 19 within the housing passageway 17. The point of contact between the shoulders 15 and 19 is predetermined so that the tip 5 of the discharge electrode is separated from the tip of the grounded electrode 4 by a precise, predetermined space or gap. This eliminates any need for manual adjustment or regapping of the electrodes. The discharge electrode assembly can then be secured in place relative to the housing 8 by means of a locking setscrew 9.

Either of the electrodes can easily be removed and replaced by reversing this process. The setscrew in the end cap 2 can be removed to allow removal of the grounded electrode 4 through the distal end of the end cap passageway 1. The discharge electrode assembly can be removed by loosening the locking setscrew 9 and unthreading the discharge electrode assembly from the interior threads 13 within the housing passageway 17. The discharge electrode assembly can then be withdrawn through the proximal opening of the housing.

The above disclosure sets forth a number of embodiments of the present invention. Other arrangements or embodiments, not precisely set forth, could be practiced under the teachings of the present invention and as set forth in the following claims.

I claim:

1. A spark gap electrode assembly for lithotripters comprising:

a grounded electrode having a base and a tip;

a housing having a passageway extending along a longitudinal axis through said housing between a distal opening and a proximal opening;

a cage extending from said housing for holding said grounded electrode base with said grounded electrode tip located in a predetermined position relative to said distal opening of said housing, said cage also including means for providing an electrical path to an external ground for said grounded electrode;

a discharge electrode assembly for removable insertion into said proximal opening of said housing having:

(a) a discharge electrode having an elongated conductive body with a proximal end for connection to an external electrical power supply and a tip at its distal end; and (b) an insulative layer covering said discharge electrode between said tip and proximal end; and stop means associated with said insulative layer and said housing passageway for preventing further insertion of said discharge electrode assembly beyond a predetermined position within said housing passageway so that said tip of said discharge electrode extends through said distal end of said housing and for fixing the distance between said tip of said discharge electrode and said tip of said grounded electrode.

2. The spark gap electrode assembly of claim 1, wherein said stop means comprises a shoulder within said housing passageway having a reduced diameter that contacts a shoulder on said insulative layer during insertion of said discharge electrode assembly into said housing passageway.

3. The spark gap electrode assembly of claim 1, further comprising threads within said housing passageway and corresponding threads on said insulative layer.

4. The spark gap electrode assembly of claim 1, further comprising means for removably securing said discharge electrode assembly within said housing passageway.

5. The spark gap electrode assembly of claim 4, wherein said means for removably securing said discharge electrode assembly comprises a setscrew extending through said housing and into said housing passageway.

6. The spark gap electrode assembly of claim 1, wherein said grounded electrode has an enlarged base, and said cage further comprises an end cap having a passageway extending through said end cap along said longitudinal axis with a stop at a predetermined location for engaging said base of said grounded electrode to ensure proper positioning of said grounded electrode tip relative to said distal opening of said housing, said end cap also having a setscrew and threads within said passageway to engage said setscrew and thereby removably secure said grounded electrode to said end cap.

7. A spark gap electrode assembly for lithotripters comprising:

a grounded electrode having an enlarged base and a tip;

a housing having a passageway extending along a longitudinal axis through said housing between a distal opening and a proximal opening, said passageway having internal threads and a stop at a predetermined location within said passageway;

a conductive end cap having a passageway extending along said longitudinal axis through said end cap for holding said base of said grounded electrode, said end cap also having a stop at a predetermined location within said passageway for engaging said base of said grounded electrode to locate said grounded electrode tip in a predetermined position relative to said distal opening of said housing;

a cage extending from said housing for supporting said end cap and grounded electrode, said cage also providing an electrical path to an external ground for said end cap and grounded electrode; and a discharge electrode assembly for removable insertion into said proximal opening of said housing having:

(a) a discharge electrode having an elongated conductive body with a proximal end for connection to an external electrical power supply and a tip at its distal end; and (b) an insulative layer covering said discharge electrode between said tip and proximal end, said insulative layer having external threads for engaging said threads within said housing passageway and a stop for contacting said stop within said housing passageway to prevent further insertion of said discharge electrode assembly beyond a predetermined position so that said tip of said discharge electrode extends through said distal end of said housing and for fixing the distance between said tip of said discharge electrode and said tip of said grounded electrode.

8. The spark gap electrode assembly of claim 7, wherein said stop within said housing passageway comprises a shoulder having a reduced diameter and said stop on said insulative layer comprises a shoulder having an increased diameter that contacts said shoulder within said housing passageway.

9. The spark gap electrode assembly of claim 7, further comprising means for removably securing said discharge electrode assembly within said housing passageway.

10. The spark gap electrode assembly of claim 9, wherein said means for removably securing said discharge electrode assembly comprises a setscrew extending through said housing and into said housing passageway.

11. The spark gap electrode assembly of claim 7, wherein said end cap further comprises a setscrew to removably secure said grounded electrode to said end cap.

12. A spark gap electrode assembly for lithotripters comprising:

a grounded electrode having an enlarged base and a tip;

a housing having a passageway extending along a longitudinal axis through said housing between a distal opening and a proximal opening, said passageway having internal threads and a shoulder with a reduced diameter at a predetermined location within said passageway;

a conductive end cap having:

(a) a passageway extending along said longitudinal axis through said end cap for holding said base of said grounded electrode with said tip extending toward said distal opening of said housing;

(b) a shoulder having a reduced diameter within said passageway at a predetermined location for engaging said base of said grounded electrode to locate said grounded electrode tip in a predetermined position relative to said distal opening of said housing; and (c) means for removably securing said base of said grounded electrode against said shoulder within said passageway of said end cap;

a cage extending from said housing for supporting said end cap and grounded electrode, said cage also providing an electrical path to an external ground for said end cap and grounded electrode;

a discharge electrode assembly for removable insertion into said proximal opening of said housing having:

(a) a discharge electrode having an elongated conductive body with a proximal end for connection to an external electrical power supply and a tip at its distal end; and (b) an insulative layer covering said discharge electrode between said tip and proximal end, said insulative layer having external threads for engaging said threads within said housing passageway and a shoulder having an increased diameter for contacting said shoulder within said housing passageway to prevent further insertion of said discharge electrode assembly beyond a predetermined position so that said tip of said discharge electrode extends through said distal end of said housing and for fixing the distance between said tip of said discharge electrode and said tip of said grounded electrode; and means for removably securing said discharge electrode assembly against said shoulder within said housing passageway.

13. The spark gap electrode assembly of claim 12, wherein said means for removably securing said discharge electrode assembly within said housing comprises a setscrew extending through said housing and into said housing passageway.

14. The spark gap electrode assembly of claim 12, wherein said means for removably securing said base of said grounded electrode to said end cap comprises a setscrew.

* * * * *